(12) United States Patent  
Tharpe, Jr.

(10) Patent No.: US 6,186,995 B1
(45) Date of Patent: Feb. 13, 2001

(54) VAGINAL TAMPON AND METHOD FOR FABRICATION THEREOF

(76) Inventor: John M. Tharpe, Jr., 1610 Louise Dr., Panama City, FL (US) 32401-1147

( * ) Notice: Under 35 U.S.C. 154(b), the term of this patent shall be extended for 0 days.

(21) Appl. No.: 09/385,905

(22) Filed: Aug. 30, 1999

(51) Int. Cl.[7] .............................. A61F 13/15; A61F 13/20
(52) U.S. Cl. ...................... 604/385.18; 604/904; 28/118
(58) Field of Search .................... 604/385.17, 385.18, 604/904, 363; 28/118

(56) References Cited

U.S. PATENT DOCUMENTS

| | | |
|---|---|---|
| Re. 28,674 | 1/1976 | Guyette . |
| 1,731,665 | 10/1929 | Huebsch . |
| 2,099,931 | 11/1937 | Fourness . |
| 2,328,795 | 9/1943 | Finks . |
| 2,710,007 | 6/1955 | Greiner et al. . |
| 3,340,874 | 9/1967 | Burgeni . |
| 3,732,866 | 5/1973 | Accacallo ............................ 604/904 |
| 4,787,895 | 11/1988 | Stokes et al. . |
| 5,366,450 | 11/1994 | DeGroot . |
| 5,800,338 | 9/1998 | Kollerup et al. ..................... 604/904 |
| 5,827,256 | 10/1998 | Balzar . |
| 5,891,123 | 4/1999 | Balzar ................................ 604/385.1 |

FOREIGN PATENT DOCUMENTS

| | | |
|---|---|---|
| 128793 | 8/1946 | (AU) . |
| 731423 | 4/1966 | (CA) . |
| 3740208A1 | 11/1987 | (DE) . |
| 515042 | 11/1939 | (GB) . |

*Primary Examiner*—Dennis Ruhl
(74) *Attorney, Agent, or Firm*—Allen, Dyer, Doppelt, Milbrath & Gilchrist, P.A

(57) ABSTRACT

A vaginal tampon and a method for fabricating same. The vaginal tampon for substantially absorbing menstrual flow includes a body having a proximal end for intravaginal positioning and a distal end for aiding in digital insertion and removal of the tampon, the body formed from a combination of an absorbent material positioned on a sheet of nonwoven material, the combination rolled together such that the absorbent material is contained within the proximal end of the vaginal tampon and the nonwoven material forms an outer surface of the body. The tampon has a head formed at the proximal end of the body from the combination of absorbent material and the sheet of nonwoven material rolled together, for substantially absorbing menstrual flow. The tampon also has a hollow tail formed at the distal end of the body from the sheet of nonwoven material rolled into an elongated hollow cylindrical member extending distally away from the head, the hollow tail allowing positioning of a finger therein for aiding in inserting and removing the tampon.

22 Claims, 7 Drawing Sheets

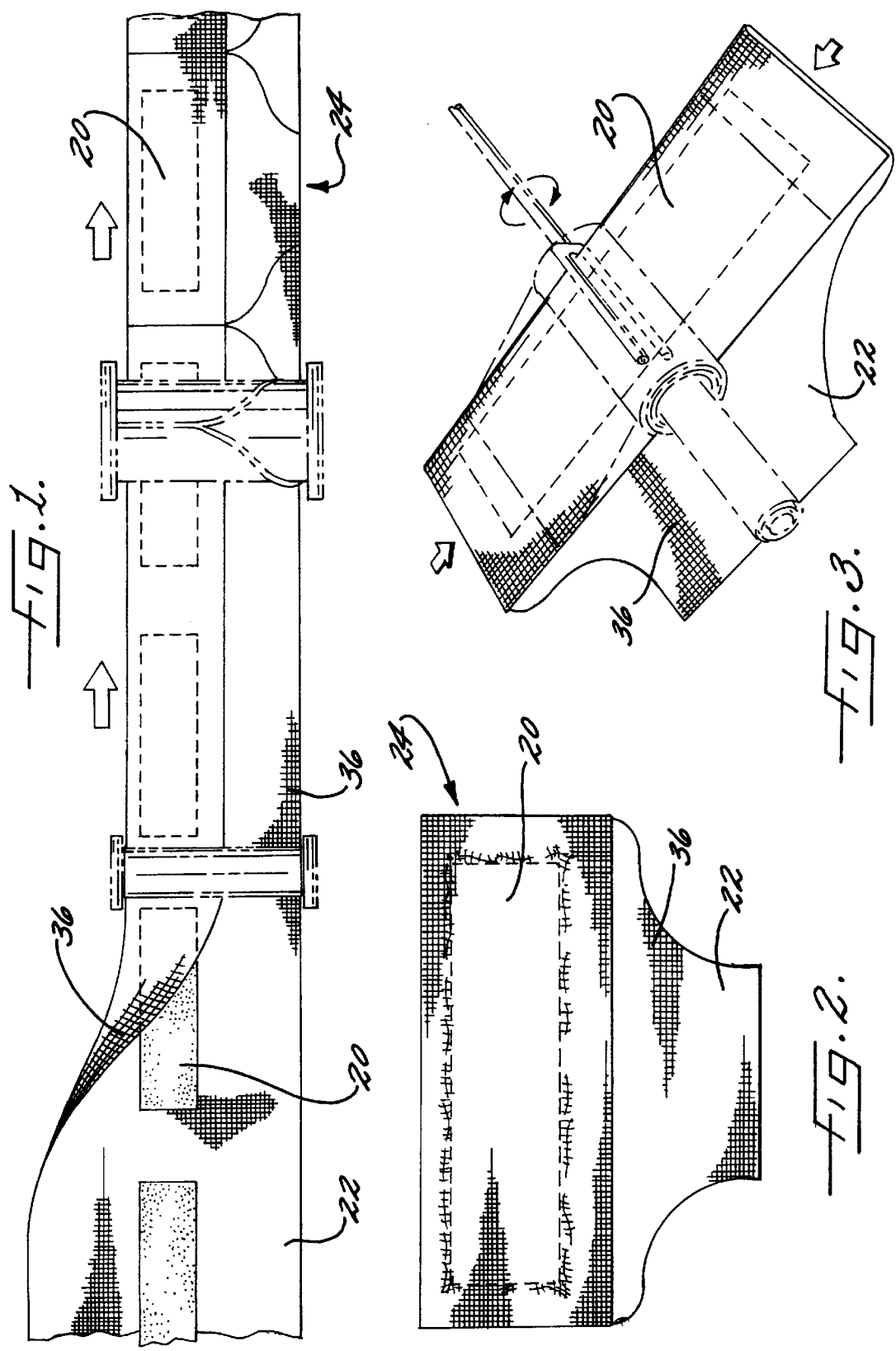

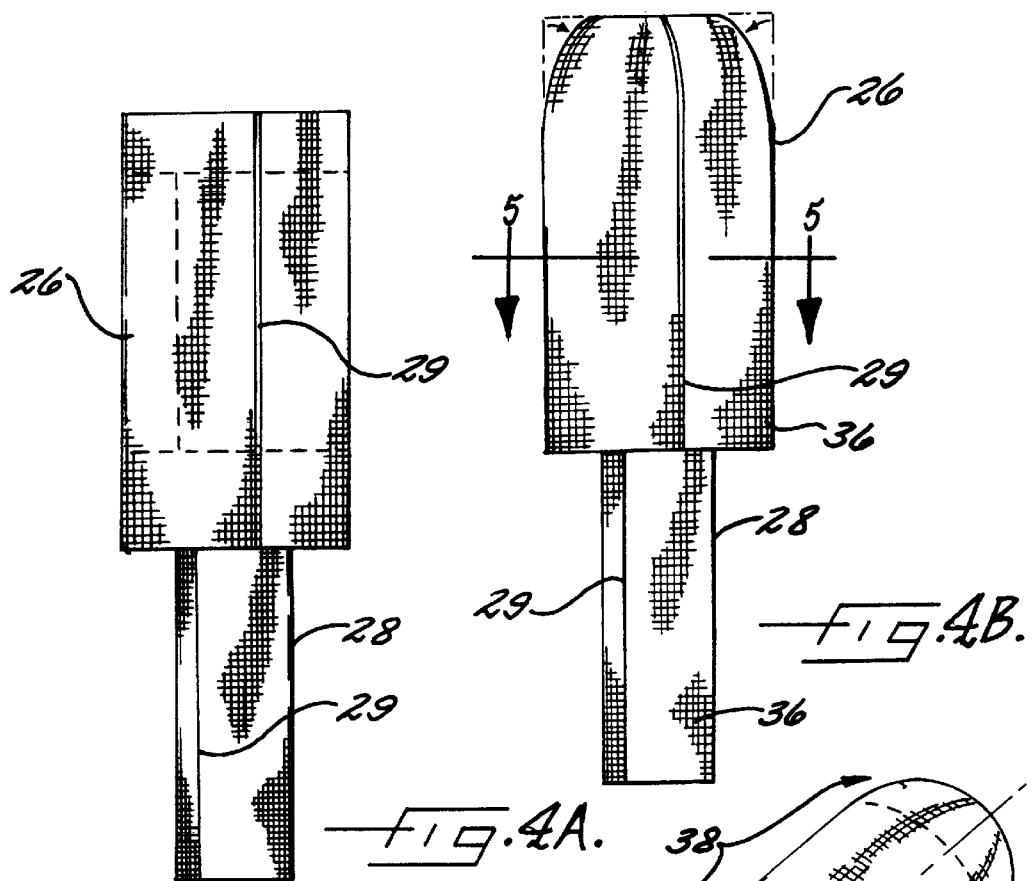
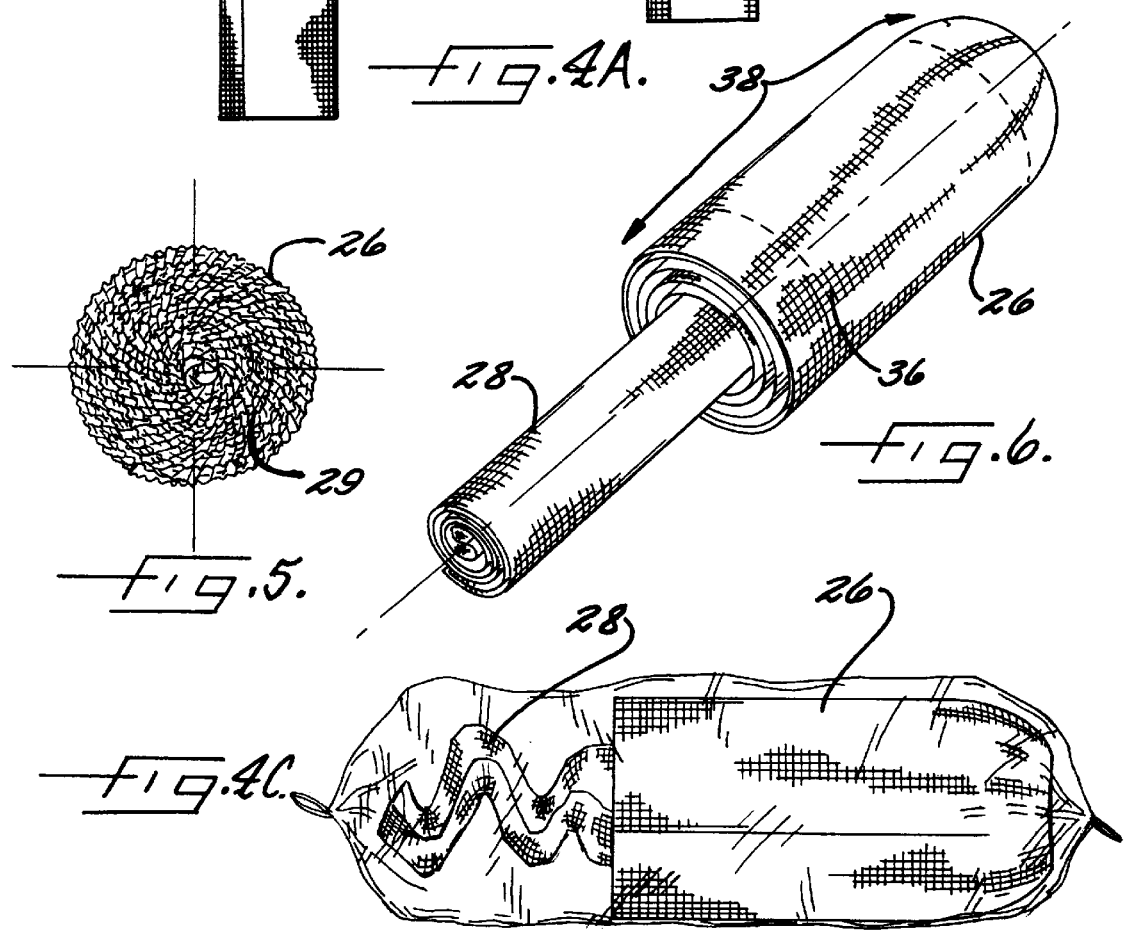

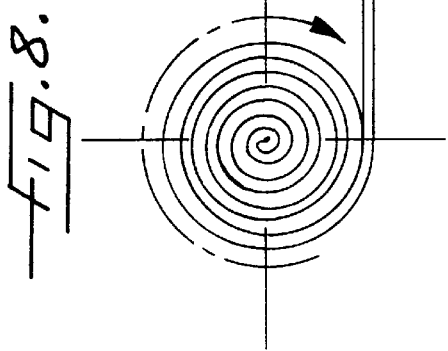
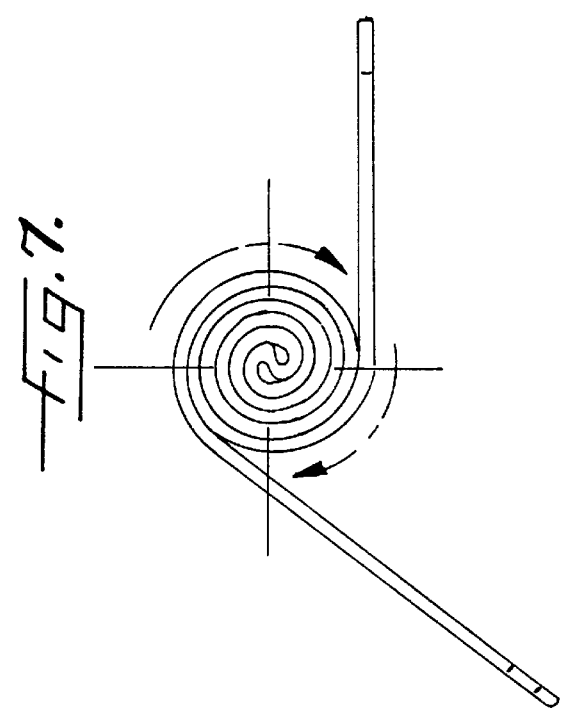
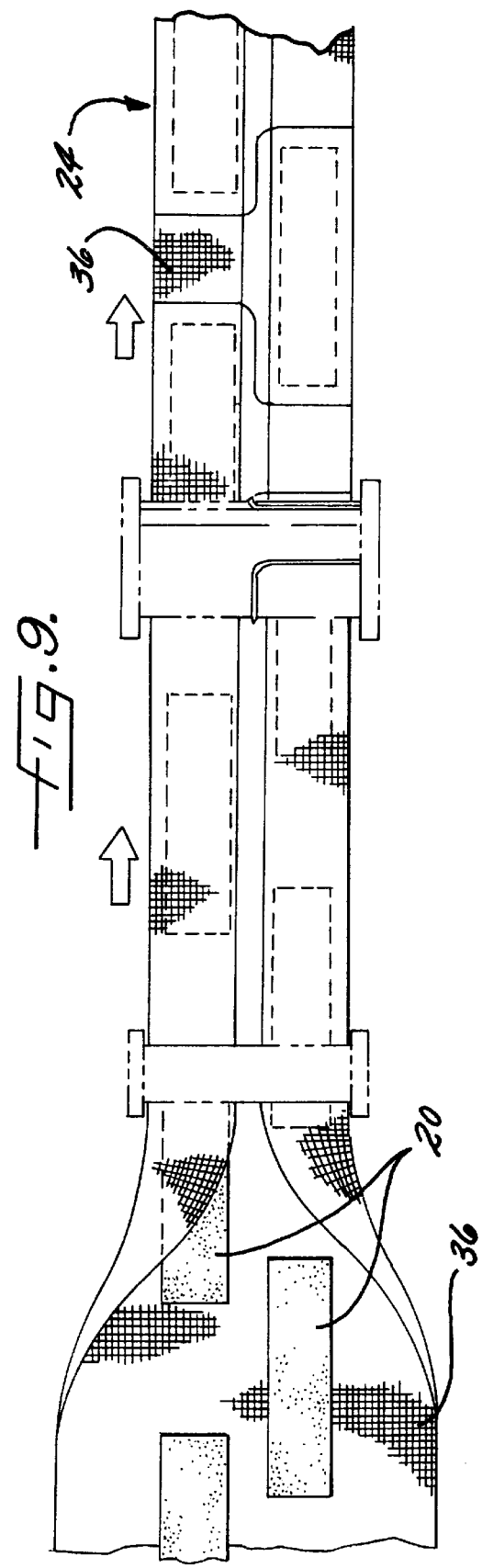

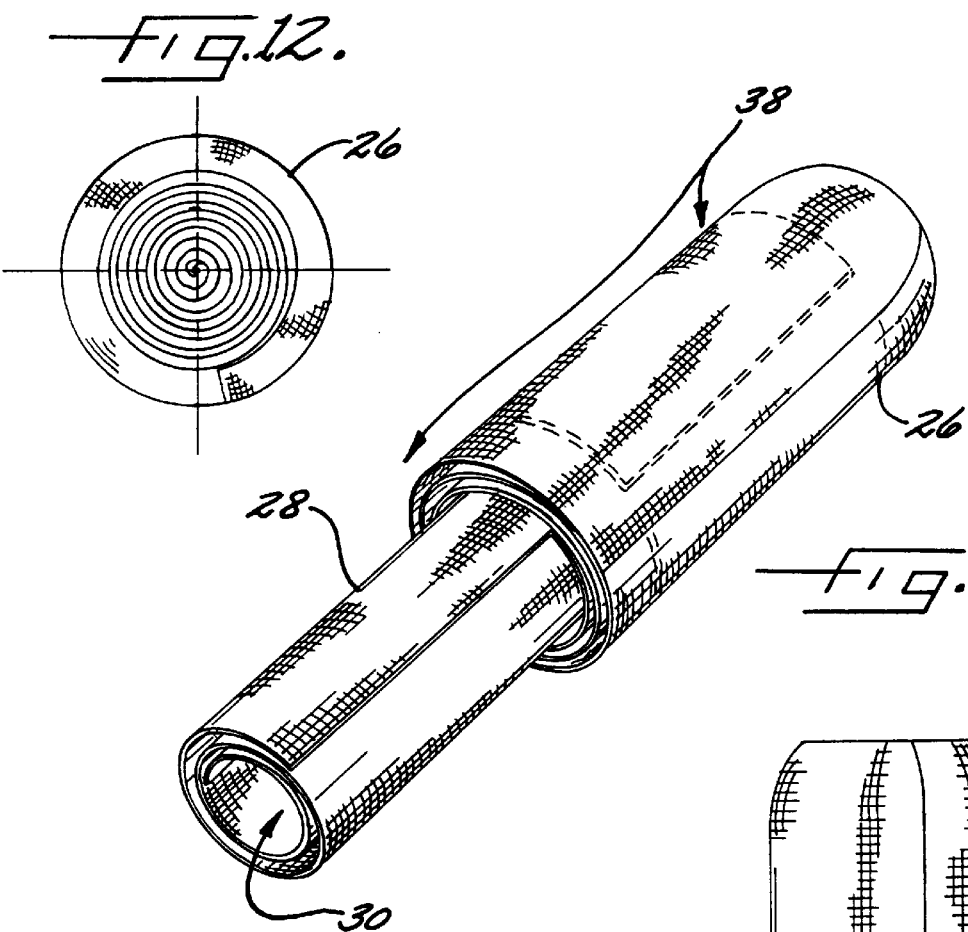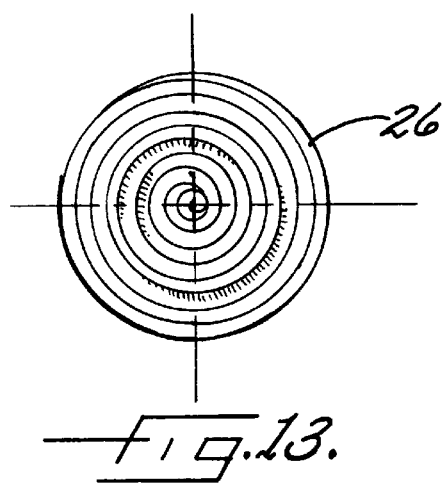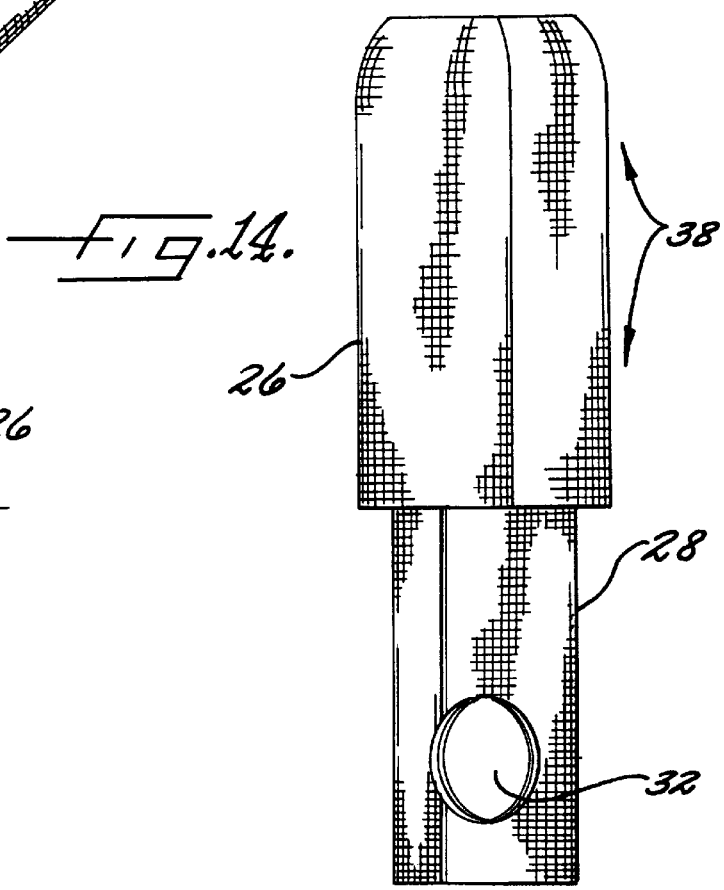

VAGINAL TAMPON AND METHOD FOR FABRICATION THEREOF

FIELD OF THE INVENTION

The present invention relates to the field of vaginal tampons and, more particularly, to vaginal tampons suitable for high-speed fabrication from a continuous sheet of material.

BACKGROUND OF THE INVENTION

Vaginal tampons are usually one of two types, those which require some type of inserter device for use, and those which may be inserted by hand, a procedure also known as digital insertion. Currently available vaginal tampons, both inserter and digital, have disadvantages. The use of tampons, in general, is plagued with various problems.

Tampons of conventional construction are known to shed and leave fibers in the vaginal canal of the user. Such fugitive fibers may provide attachment places for microorganisms, and thereby may serve to promote their overgrowth in the vagina, with potential adverse consequences for the user.

The use of a string for effecting removal of the vaginal tampon is an additional source of problem. The string is difficult to securely attach to the tampon during manufacture. Attachment of the string to the absorbent material is often a rate limiting step in the manufacturing process. Current tampon manufacturing production rates are usually in the range of 150 to 700 tampons per minute. In addition, the string may detach while the user is attempting removal of the tampon, creating at the very least an annoying problem. A popular vaginal tampon in current use is made of a large cotton batting, with a string sewn onto the batting. The batting is then rolled into a tampon shape, compressed, and either wrapped for digital insertion or combined with an inserter. This popular design embodies the various problems highlighted above.

Moreover, inserter type vaginal tampons are expensive to manufacture, particularly because of the added materials, processing and cost attributable to the inserter device. Further, disposal of the inserter device has become an environmental issue, not only because of the added trash volume which it contributes, but also due to associated concerns related to disposal of articles contaminated with body fluids.

Tampons constructed from absorbent materials rolled up in a nonabsorbent material have been known in the art. Most of these tampons have also incorporated a string device connected to the absorbent body of the tampon for use in removal of the device. Tampon rolls having this design may suffer from the unfortunate tendency to unroll as they are pulled from the vagina for disposal. When the user pulls on the string, the tampon roll tends to unwind, or "telescope", producing an elongated, twisted, unsightly result which is a mess to handle and is difficult to remove.

Newer, super absorbent vaginal tampons are designed so that they form an effective seal when properly positioned within the vaginal canal. This effective seal ensures essentially little or no leakage of menstrual flow to the outside. Such an effective seal, however, may prove to be irritating to the vaginal epithelium of some users. Combined with this enhanced absorbent quality, the effective leak prevention has encouraged some users to leave these tampons in place for extended periods of time, a contributing factor which may lead to a medical condition known as toxic shock syndrome.

Toxic shock syndrome is now known to be caused by an overgrowth of toxin secreting strains of *Staphylococcus aureus*, a bacterium which may sometimes be found in the vaginal flora of otherwise healthy menstruating women. Because toxic shock syndrome is caused by the staphylococcal toxin, which is produced in greater amounts during overgrowth of these bacteria, it has been theorized that changing tampons at least once every 24 hours, rather than leaving the tampon in place for an extended time, could help reduce the bacterial overgrowth, and thus help prevent toxic shock syndrome. In fact, this observation has proved correct, and implementation of the recommended practice of changing tampons daily has reduced the incidence of this condition.

SUMMARY OF THE INVENTION

With the foregoing in mind, the present invention provides a vaginal tampon having a hollow tail useful both in digital insertion and in removal of the tampon. The hollow tail is formed by a sheet of nonwoven material which is an integral structural component of the tampon and is not a separate component which must be connected thereto, such as a string sewn onto a tampon of conventional design. The hollow tail of the present tampon invention provides various advantages. Elimination of the string produces a tampon which is substantially resistant to unwinding and to breakage during removal. The hollow tail allows positioning of a finger therein for aiding in digital insertion of the tampon. In this procedure, the user's finger is essentially protected from direct contact with menstrual discharges during insertion of the tampon. In addition, in one embodiment of the invention the hollow tail has an opening positioned transversely therethrough, preferably near the distal end of the tail, for providing a grasping place for aiding in digital removal of the tampon.

The present invention further provides a vaginal tampon of overall construction suitable for manufacturing by a method which may be implemented in a high speed production line at production rates not previously achieved for tampons. Such a method of manufacturing the vaginal tampon of the present invention includes the step of forming a continuous absorbent pad by positioning an absorbent material on spaced-apart portions of a continuous sheet of nonwoven material moving along a direction of manufacture. The continuous absorbent pad is next divided into a plurality of individual absorbent pads. Each absorbent pad is then rolled so as to form a tampon roll having a head positioned at a proximal end of the tampon roll and a tail positioned at a distal end of the tampon roll. The head is formed by the portion of the sheet of nonwoven material having the absorbent material positioned thereon, so that the sheet of nonwoven material forms an outer surface of the head. The tail is an elongated member having a hollow center and extending distally away from the head. The hollow tail is formed by that portion of the sheet of nonwoven material having no absorbent material positioned thereon, the hollow center allowing positioning of a finger therein for aiding in inserting and removing the tampon. Lastly, the tampon roll is molded so as to form a head having a shape suitable for promoting digital insertion of the tampon. The tampon roll produced by this method of manufacture has sufficient structural strength for digital insertion, eliminating the need for an inserter. In addition, this method of manufacturing allows for production rates of up to approximately 2000 tampons per minute, resulting in greatly reduced per unit production cost.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 1 is a schematic diagram of a production method according to an embodiment of the present invention;

FIG. 2 shows a folded absorbent pad before rolling;

FIG. 3 schematically illustrates a method of rolling the tampon;

FIG. 4 shows a rolled tampon before shaping(4A), after shaping (4B), and wrapped for packaging (4C);

FIG. 5 is a cross section of a tampon roll formed as a single roll;

FIG. 6 shows a perspective view of a tampon after shaping;

FIG. 7 schematically shows a method for rolling a tampon into a double roll;

FIG. 8 schematically shows a method for rolling a tampon into a single roll;

FIG. 9 is a schematic view of another preferred production method;

FIG. 11 shows a shaped tampon having a hollow tail;

FIG. 12 is a top plan view of the shaped tampon from the proximal end;

FIG. 13 is a bottom plan view of the shaped tampon from the distal end;

FIG. 14 illustrates a shaped tampon having an opening transversely positioned in the hollow tail;

DETAILED DESCRIPTION

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. The vaginal tampon and the method for its fabrication are shown in FIGS. 1 through 17.

Figure 10B:
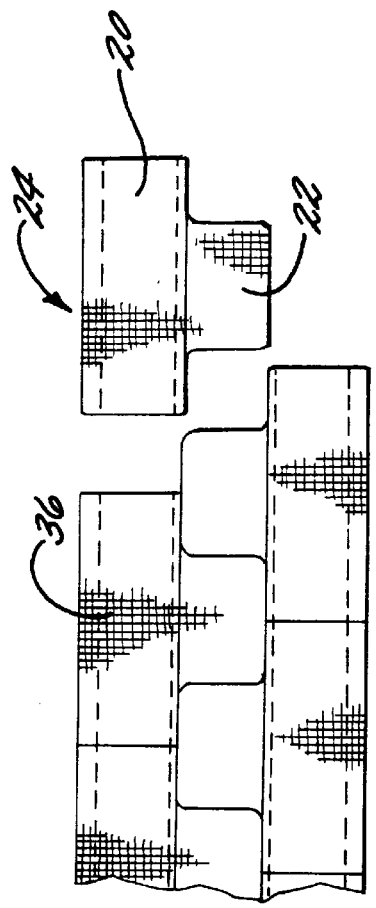
FIG. 10 (10A and 10B) shows a schematic diagram of a method for production of interlocked absorbent pads.
Figure 10A:
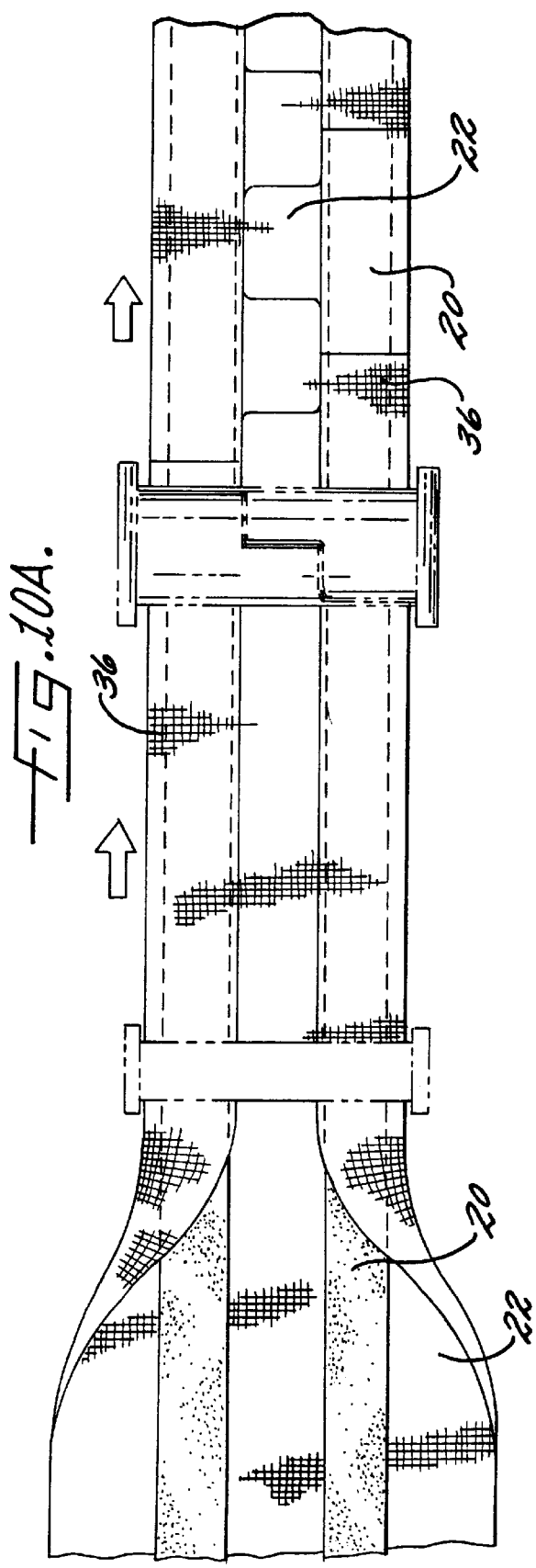

FIG. 1 illustrates a production line method for manufacturing vaginal tampons, particularly showing the manufacturing process of the present invention. The method of forming a plurality of vaginal tampons includes forming a continuous stream of a plurality of absorbent pads by layering a continuous stream of absorbent material on spaced-apart portions of a continuous sheet of nonwoven material moving along a path of manufacture, as known to those skilled in the art. The absorbent material 20 and the nonwoven material 22 may generally include hydrophilic fibers preferably of a cellulosic material such as viscose fiber or cotton, but may be of any material known to the skilled artisan to be safe and effective for such use in a tampon. The absorbent material 20 may be positioned on the continuous sheet of nonwoven material 22 as individual strips of the absorbent material 20, as shown in FIGS. 1, 2, 3 and 9, 15 and 16, or as at least one and preferably two continuous strips 34 of absorbent material 20, as shown in FIGS. 10A and 10B. Downstream from the absorbent pad forming step, the continuous stream of absorbent pad is divided into individual absorbent pads 24, as best shown in FIGS. 1, 9 and 10. Each individual absorbent pad 24 is then rolled on itself, as shown schematically in FIG. 3, for forming a vaginal tampon roll. The tampon roll is formed so that it has a spiral cross section configuration, as best shown in FIGS. 3, 5, 7, 8, 12, 13 and 16. The absorbent pad 24 is rolled such that, in cross section, the portion of the sheet of nonwoven material having the absorbent material thereon forms the head 26 of the tampon, having the sheet of nonwoven material as the outer surface of the head, as shown in FIGS. 4, 6, 11 and 14. As the absorbent pad is rolled, a remaining portion of the sheet of nonwoven material extends away from the head of the tampon to form an elongated tail 28, also illustrated in FIGS. 3, 6 and 10.

The tail 28 is formed so that it has a longitudinal dimension and a hollow center 30 for aiding digital insertion and removal of the vaginal tampon. The head 26 of the tampon is formed at a proximal portion of the vaginal tampon, the proximal portion being that part of the tampon intended to be first inserted vaginally. The tail 28 of the tampon is formed at a distal portion of the vaginal tampon by the sheet of nonwoven material 22 extending distally away from the head 26 of the vaginal tampon. The head and tail arrangement of the vaginal tampon is best shown in FIGS. 4, 6, 11 and 14. After rolling the absorbent pad, the head 26 of the vaginal tampon is then shaped by a shaper, or mold, as known to those skilled in the art. Shaping takes place downstream from the rolling step, and is carried out to form a head 26 having a substantially rounded end, thereby to ease insertion of the vaginal tampon, as shown in FIGS. 6, 11 and 14.

Other preferred embodiments of the method include a bonding step as known to those skilled in the art, for bonding the vaginal tampon roll, thereby to essentially prevent the vaginal tampon roll from unrolling during use. Bonding may be accomplished through application of a non-allergenic, water resistant adhesive, through a heat or ultrasonic sealer, or by use of other known methods and materials. The bonding of the vaginal tampon roll is preferably localized along the outer edge of the formed roll, as illustrated in a view of the edge 29 on the formed vaginal tampon shown in FIGS. 4A, 4B and 5.

In yet another preferred embodiment of the method, the vaginal tampon may be further formed having an opening 32 transversely positioned through the tail, thereby to provide a grasping place for aiding in digital removal of the vaginal tampon. The step of making the opening may be accomplished by use of a hole maker, such as a drill or similar hole making device as known in the art, the device positioned downstream from the absorbent pad former. In a preferred embodiment of the method, the opening may be formed preferably by a die cutter as the absorbent pad moves along the production line. Alternatively, the opening may be formed through the tail after the absorbent pad is rolled to form the vaginal tampon, as shown in FIGS. 14 and 17.

In an additional embodiment of the method, the continuous sheet of nonwoven material is preferably a fenestrated material 36, that is, the material includes a plurality of small perforations, as shown throughout the figures. It is desirable that in this step the sheet of nonwoven material be sufficiently perforated to thereby promote increased passage of body fluids through the material for absorption by the absorbent pad forming the head of the vaginal tampon. The material may be fenestrated at manufacture or, alternatively, the step of perforating the sheet of nonwoven material may be accomplished during manufacture of the tampon by a perforator, such as a roller having protrusions for perforating material, or other perforating means known in the art.

Figure 17:
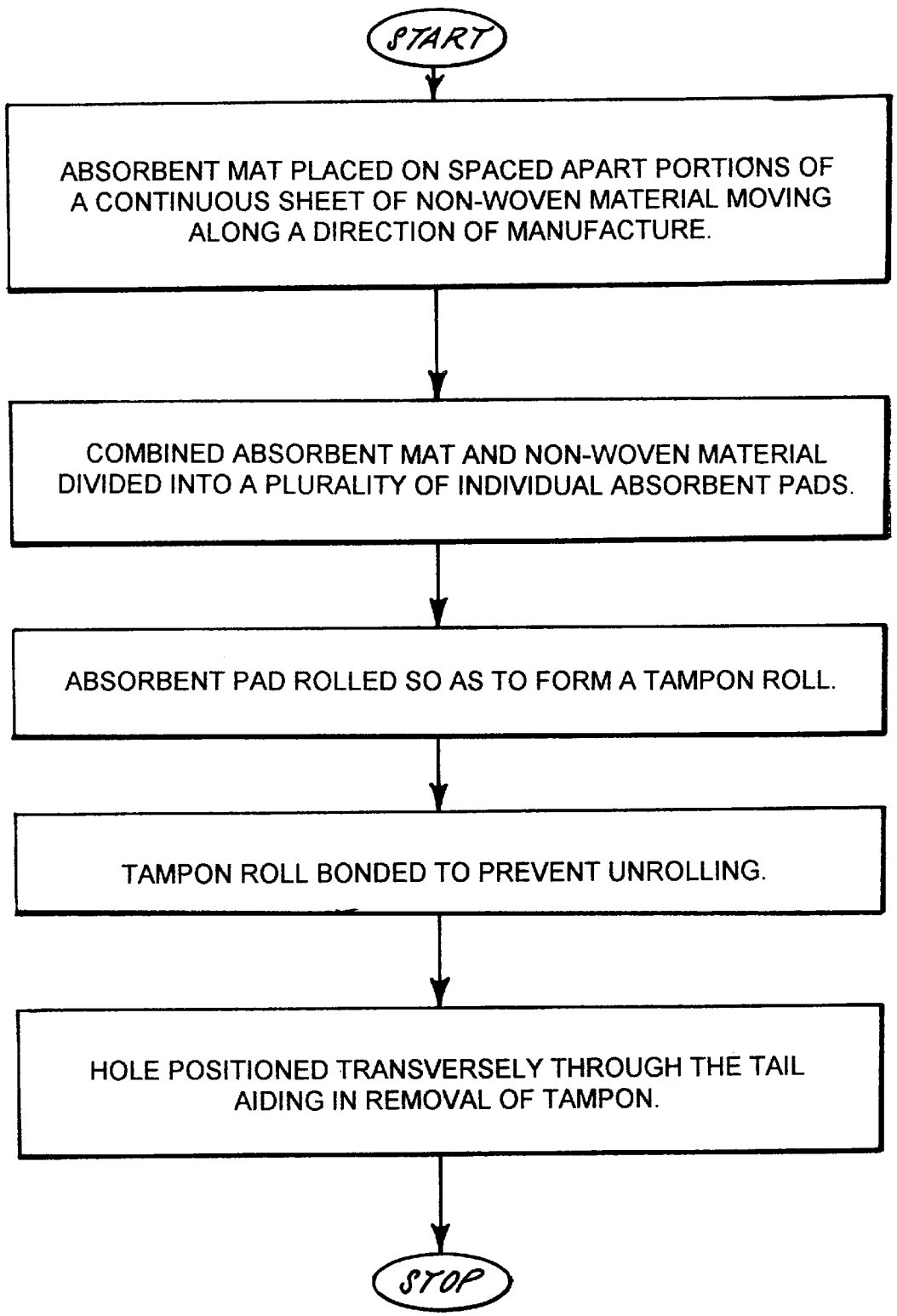
FIG. 17 is a block diagram illustrative of a preferred method for making the vaginal tampon of the present invention.

To increase the durability of the vaginal tampon, the absorbent pad forming step may further include an absorbent pad bonding step for bonding the absorbent material to the continuous sheet of nonwoven material, as shown in FIG. 17. Preferably, the absorbent pad may be spot bonded at its edges to the underlying sheet of nonwoven material. However, the pattern of bonding may be varied, depending on the characteristics of the bonding technique employed. A preferred bonding material is a non-allergenic, water resistant adhesive, so that it does not become weak when exposed to menstrual fluids. Examples of suitable bonding materials include polyester films and a variety of adhesives applied hot as a flowing melt, or as a powder, such as polypropylene. A preferred adhesive for hot application would be, for example, ethylene-vinyl acetate resin. In addition, thermal or ultrasonic sealing of the tampon roll may also be accomplished by methods known in the art.

Figure 15:
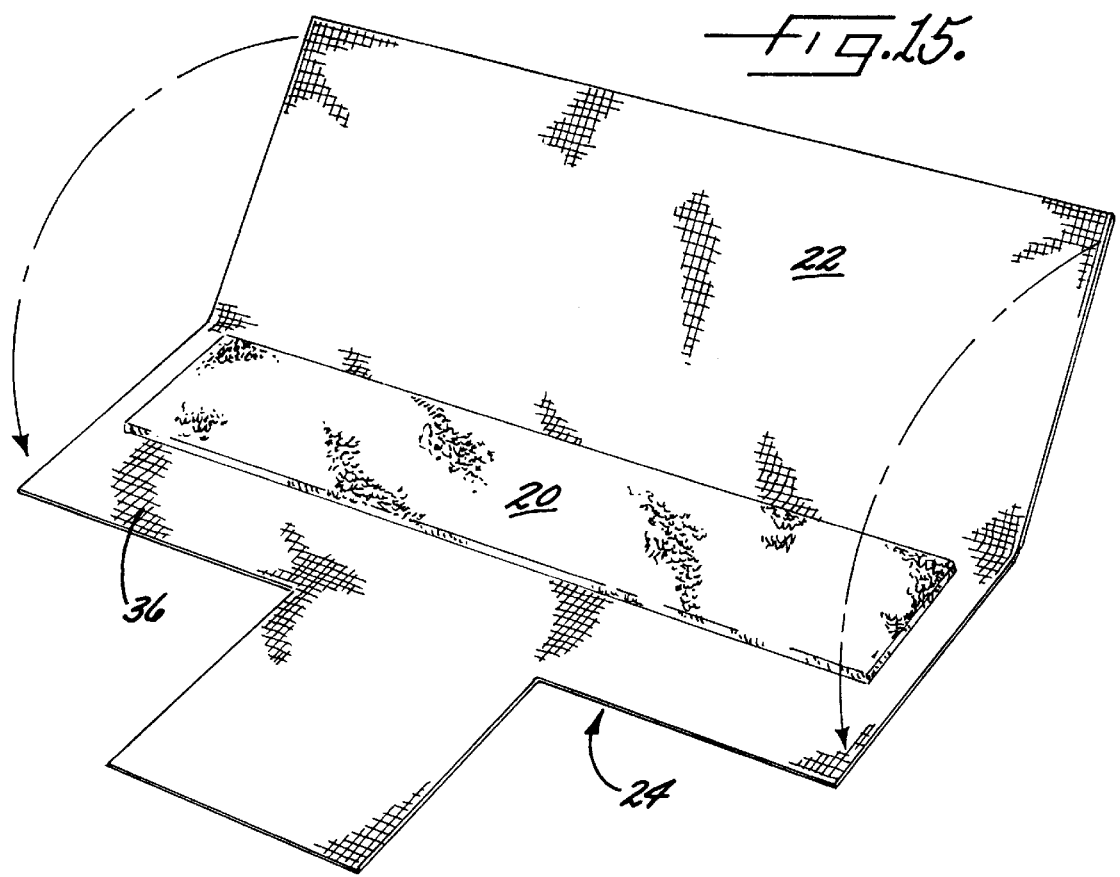
FIG. 15 schematically shows a method of folding a layer of nonwoven material over an absorbent material.
Figure 16:
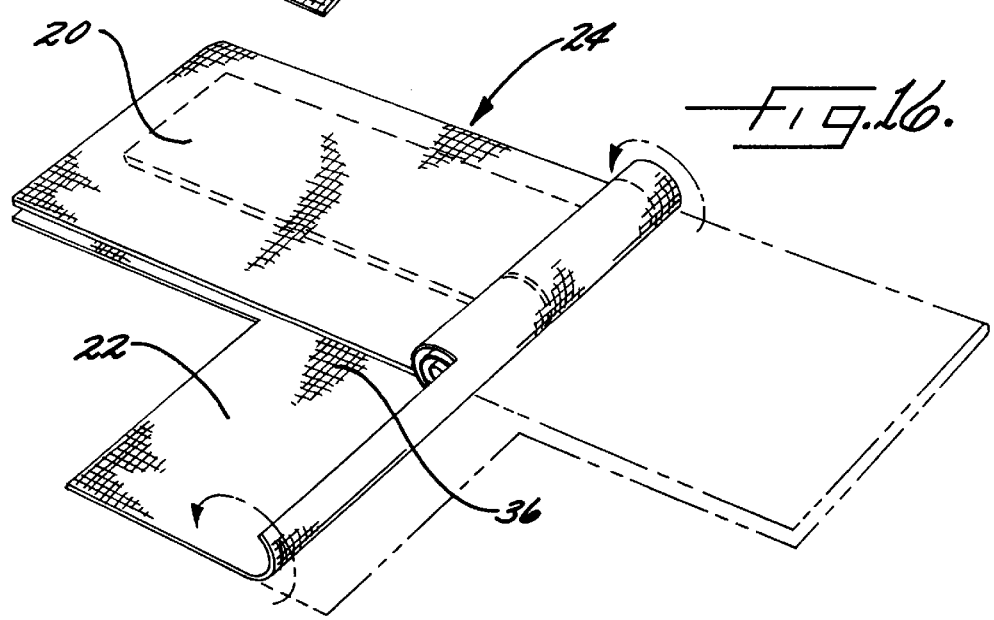
FIG. 16 shows a method of rolling a tampon rolls.

In another preferred embodiment of the invention the vaginal tampon forming method also includes a sheet folding step, the folding accomplished by means known in the art, as shown in FIGS. 1, 9, 10 and 15. The sheet folding step is positioned downstream from the absorbent pad forming step, and serves to fold an edge portion of the continuous sheet of nonwoven material 22 over the absorbent material 22, as also shown in FIG. 15, thereby aiding in securely containing the absorbent material as the tampon roll is formed, as seen in FIG. 16.

A particularly advantageous method for high-speed production of the vaginal tampons is shown in FIGS. 10A and 10B. The vaginal tampon production process may be configured in this preferred embodiment such that the pad forming step further includes positioning a plurality of continuous strips 34 of absorbent material on the continuous sheet of nonwoven material 22 moving along a path of manufacture, to thereby form a plurality of absorbent material streams on the continuous sheet of nonwoven material, as best seen in FIG. 10A. Means for positioning a plurality of continuous strips 34 of material onto a moving sheet are known and used in the art, particularly in relation to disposable undergarments. In such configuration, the vaginal tampon production process further includes the step of dividing the plurality of absorbent material streams into a plurality of individual absorbent pads 24, as shown schematically in FIG. 10B. This is a highly efficient step which produces interlocked absorbent pads and utilizes the entire available surface of the continuous sheet of nonwoven material, as seen particularly in FIG. 10B. This high throughput production process, shown schematically in FIGS. 10A and 10B, is estimated to produce approximately up to 2000 tampons per minute, at a normal production speed. Vaginal tampon rolls made from the absorbent pads produced in this fashion may also be bonded to substantially prevent unrolling, may be provided with a hole in the tail to aid in digital removal, may include a perforated sheet of nonwoven material folded over the absorbent material to promote absorption of body fluids, and may also have the absorbent material bonded to the sheet of nonwoven material, as previously described above, to aid in maintaining the integrity of the tampon during use.

The present invention includes the vaginal tampon 38 product manufactured by the above described method, and shown in FIGS. 6, 11 and 14. The vaginal tampon 38 has a proximal end and a distal end, as these terms are defined above. The proximal end of the vaginal tampon 38 includes a head 26, which serves for insertion and for substantially absorbing menstrual flow. The head 26 is generally formed from a combination of a layer of absorbent material 20 and a sheet of nonwoven material 22 by rolling the combination together such that the sheet of nonwoven material 22 forms the outer surface of the head 26. The distal portion of the vaginal tampon 38 includes the tail 28, which is an elongated member having a hollow center 30, for aiding digital insertion and removal of the vaginal tampon 38. The tail 28, also shown in FIGS. 4, 6, 11 and 14, is elongated and is formed at the distal end of the vaginal tampon 38 by the rolled sheet of nonwoven material 22 extending distally from the proximal portion of the vaginal tampon 38, the tail part of the vaginal tampon including no absorbent material 20. Once rolled, the vaginal tampon 38 is shaped to preferably include a head 26 having a substantially rounded end for promoting ease of insertion, as shown in FIGS. 4, 6, 11 and 14. In another preferred embodiment the tail has an opening 32 transversely therethrough, the opening being positioned to provide a grasping place for aiding in digital removal of the vaginal tampon. The opening may be formed on the production line or may be formed after the tampon is rolled.

In yet another preferred embodiment of the tampon product 38, the nonwoven material is perforated 36 sufficiently to thereby promote increased passage of body fluids through the nonwoven material for absorption by the layer of absorbent material 20, as shown throughout the figures. Additionally, in a further embodiment of the invention the layer of absorbent material 20 is bonded to the nonwoven material 22, thereby to aid in maintaining the integrity of the vaginal tampon 38 during use. The vaginal tampon may also include an absorbent pad wherein an edge portion of the sheet of nonwoven material 22 is folded over the layer of absorbent material 20, thereby to aid in securely containing the layer of absorbent material within the tampon roll, as shown in FIGS. 2 and 15.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A vaginal tampon for substantially absorbing menstrual flow, said tampon comprising:

a tampon roll comprising absorbent material and a first sheet portion of a sheet of nonwoven material, said tampon roll defining a proximal end of said tampon; and a hollow tail extending distally from said tampon roll said hollow tail comprising a second sheet portion of said sheet of nonwoven material, said second sheet portion extending medially and substantially perpendicularly from said first sheet portion;

wherein the absorbent material is positioned substantially on the first sheet portion, the absorbent material and sheet of nonwoven material being rolled together so as to form the tampon roll substantially from the first sheet portion, and so as to form the hollow tail substantially from the second sheet portion.

2. The tampon of claim 1, wherein the tampon is shaped so that the tampon roll has a substantially cylindrical shape having a lateral circumferential periphery, a substantially rounded upper periphery positioned at the proximal end, and a lower periphery connected to said hollow tail.

3. The tampon of claim 1, wherein said hollow tail has an opening positioned transversely therethrough to thereby provide a grasping place for aiding removal of the tampon.

4. The tampon of claim 1, wherein the sheet of nonwoven material comprises fenestrations for aiding the passage of menstrual flow therethrough.

5. The tampon of claim 4, wherein the fenestrations are substantially limited to a portion of the sheet of nonwoven material forming the tampon roll.

6. The tampon of claim 1, wherein the absorbent material is bonded to the sheet of nonwoven material to thereby aid in preventing the tampon roll from unrolling.

7. The tampon of claim 1, wherein a portion of the sheet of nonwoven material is folded over the absorbent material before the combination is rolled together to thereby aid in containing the absorbent material within the tampon.

8. A vaginal tampon for substantially absorbing menstrual flow, said tampon comprising:
- a sheet of nonwoven material having a first sheet portion including a lengthwise extent, and having a second sheet portion extending medially from said first sheet portion and substantially perpendicularly to said lengthwise extent so as to define a "T" shape; and
- an absorbent material positioned substantially on the first sheet portion;
- wherein the absorbent material and sheet of nonwoven material are rolled together to form a tampon roll defining a proximal end of said tampon, and to form a tampon tail from the second sheet portion, defining a distal end of said tampon.

9. The tampon of claim 8, wherein the tampon roll has a substantially cylindrical shape for vaginal insertion, having a lateral circumferential periphery and a substantially rounded upper periphery at the proximal end, and wherein the tampon tail forms a lower periphery of said tampon.

10. The tampon of claim 8, wherein said tail has an opening positioned transversely therethrough to thereby provide a grasping place for aiding removal of the tampon.

11. The tampon of claim 8, wherein the sheet of nonwoven material comprises fenestrations for aiding the passage of menstrual flow therethrough.

12. The tampon of claim 11, wherein said fenestrations are substantially limited to the first sheet portion of the nonwoven material.

13. The tampon of claim 8, wherein the absorbent material is bonded to the sheet of nonwoven material to thereby aid in preventing the tampon roll from unrolling.

14. The tampon of claim 8, wherein a portion of the sheet of nonwoven material is folded over the absorbent material before the combination is rolled together to thereby aid in containing the absorbent material within the tampon.

15. A method of manufacturing a vaginal tampon, the method comprising:

a) forming a continuous absorbent pad by positioning a continuous absorbent material on at least a portion of a continuous sheet of nonwoven material;

b) dividing the continuous absorbent pad into a plurality of individual absorbent pads;

c) rolling each individual absorbent pad of said plurality so as to form a tampon having a tampon roll positioned at a proximal end and a tail positioned at a distal end, the tampon roll formed by the at least a portion of the continuous sheet of nonwoven material having the absorbent material positioned thereon so that the sheet of nonwoven material forms an outer surface of the roll, the hollow tail formed as an elongated member having a substantially hollow center and extending distally from the tampon roll, the hollow tail formed by a portion of the sheet of nonwoven material having substantially no absorbent material positioned thereon, wherein the hollow center allows positioning of a finger therein for aiding in inserting and removing the tampon; and d) shaping the tampon to provide a tampon roll having a substantially rounded proximal end for aiding insertion of the tampon.

16. The method of claim 15, further comprising bonding the absorbent material to the continuous sheet of nonwoven material to thereby aid in preventing the tampon roll from unrolling.

17. The method of claim 15, further comprising positioning a hole transversely through the tail, to thereby provide a grasping place for aiding removal of the tampon.

18. The method of claim 15, further comprising sufficiently fenestrating the nonwoven material to thereby aid passage of menstrual flow therethrough.

19. The method of claim 15, further including the step of folding at least a portion of the continuous sheet of nonwoven material over the absorbent material prior to dividing the continuous absorbent pad, to thereby aid in containing the absorbent material within the tampon roll.

20. The method of claim 15, wherein the dividing step comprises dividing the continuous absorbent pad into individual absorbent pads each having the absorbent material positioned substantially along a first portion of the absorbent pad having a lengthwise extent positioned substantially parallel to a direction of manufacture, and so that a second portion of each individual absorbent pad is connected to about a midpoint of the lengthwise extent of the first portion and extends substantially perpendicularly therefrom.

21. The method of claim 15, wherein the absorbent material is positioned on the continuous sheet of nonwoven material as the sheet moves along a direction of manufacture.

22. The method of claim 15, wherein the continuous absorbent pad is divided into the plurality of individual absorbent pads while moving along a direction of manufacture.

* * * * *